US010502746B2

(12) United States Patent
Stubenrauch et al.

(10) Patent No.: US 10,502,746 B2
(45) Date of Patent: Dec. 10, 2019

(54) SPECIFIC DETECTION OF RAT ANTIBODIES IN MOUSE SERUM

(71) Applicant: Hoffmann-La Roche Inc., Little Falls, NJ (US)

(72) Inventors: Kay-Gunnar Stubenrauch, Penzberg (DE); Uwe Wessels, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 770 days.

(21) Appl. No.: 14/858,449

(22) Filed: Sep. 18, 2015

(65) Prior Publication Data

US 2016/0077100 A1  Mar. 17, 2016
US 2016/0266135 A2  Sep. 15, 2016
US 2017/0370941 A2  Dec. 28, 2017

Related U.S. Application Data

(63) Continuation of application No. PCT/EP2014/055462, filed on Mar. 19, 2014.

(30) Foreign Application Priority Data

Mar. 20, 2013 (EP) ..................... 13160143

(51) Int. Cl.
*G01N 33/68* (2006.01)
*G01N 33/94* (2006.01)

(52) U.S. Cl.
CPC ....... *G01N 33/686* (2013.01); *G01N 33/6854* (2013.01); *G01N 33/94* (2013.01)

(58) Field of Classification Search
None
See application file for complete search history.

(56) References Cited

U.S. PATENT DOCUMENTS 5,332,665 A     7/1994  Reed et al.
6,306,626 B1 *  10/2001 Rosenblum ........ A61K 47/6873
                                                   424/178.1

FOREIGN PATENT DOCUMENTS

| EP | 0 978 287 A1 | 2/2000 |
| EP | 1365243 | 2/2004 |
| JP | 62-257395 | 11/1987 |
| JP | 7-502019 | 2/1993 |
| JP | 6-113830 | 4/1994 |
| JP | 2004-045384 A | 11/2003 |
| JP | 2012-526846 | 11/2010 |
| WO | WO 93/02693 | 3/1995 |
| WO | 95/33204 A1 | 12/1995 |
| WO | 2005/045058 A2 | 5/2005 |
| WO | 2006/066912 A2 | 6/2006 |
| WO | 2008/031532 A1 | 3/2008 |
| WO | 2011/048043 A1 | 4/2011 |
| WO | WO 2010/132683 | 11/2012 |

OTHER PUBLICATIONS

Kremmer et al., "Monoclonal Antibodies to Complement Components Without the Need of Their Prior Purification. II. Antibodies to Mouse C3 and C4" Hybridoma 9(4):309-317 (Aug. 1990).
Li et al., "Preparation and Identification of the Rat Antibody Against Recombinant Buckwheat Trypsin Inhibitor" Xi Bao Yu Fen Zi Mian Yi Xue Za Zhi (Article in Chinese. Submitting the Abstract), 25(6):513-515 (Jun. 2009).
Brodin, N. et al., "Use of a monoclonal rat anti-mouse Ig light chain (RAMOL-1) antibody reduces background binding in immunohistochemical and fluorescent antibody analysis" The Journal of Histochemistry and Cytochemistry 37(7):1013-1024 (Jul. 1, 1989).
Hansen, R et al., "An ELISA for quantification of murine IgG in rat plasma: application to the pharmacokinetic characterization of AP-3, a murine anti-glycoprotein IIIa monoclonal antibody, in the rat" Journal of Pharmaceutical and Biomedical Analysis 21(5):1011-1016 (Dec. 1, 1999).
Pearce-Pratt, R, "False-positive signals in enzyme immunoassay ( EIA) interactions between rodent IgG subclasses" Journal of Immunological Methods 130(1):65-72 (Jun. 12, 1990).
Stubenrauch, K et al., "Evaluation of an immunoassay for human-specific quantitation of therapeutic antibodies in serum samples from non-human primates" Journal of Pharmaceutical and Biomedical Analysis 49(4):1003-1008 (May 1, 2009).
WO 2014/147101 A1, Publication of International Application No. PCT/EP2014/055462 (Sep. 25, 2014).
Komuro, Katsutoshi et al., "Prevention and treatment of infection" Rinsho-menneki 18(10):193-201 ( 1986).
Sado, Yoshikazu et al., "Production of polyclonal and monoclonal antibodies against IgG of suncus murinus, house musk shrew" The Shigei Medical Journal (English Abstract), 32:3-13 ( 2010).

\* cited by examiner

*Primary Examiner* — Changhwa J Cheu
(74) *Attorney, Agent, or Firm* — Jonathan P. Aumais

(57) ABSTRACT

One aspect as reported herein is a method for detecting a rat antibody in a serum or plasma sample (obtained) from a mouse comprising the steps of
  a) providing the sample to be analyzed,
  b) incubating said serum or plasma sample with an antibody that specifically binds to rat IgG and that does not specifically bind to mouse IgG,
    wherein the antibody is
    i) a mixture of an antibody binding to rat kappa light chain and an antibody binding to rat lambda light chain, or
    ii) a mixture of an antibody binding to rat IgG1 with an avidity of $4.1 \times 10^{10}$ $M^{-1}$ or more, an antibody binding to rat IgG2a with an avidity of $8.6 \times 10^{9}$ $M^{-1}$ or more, an antibody binding to rat IgG2b with an avidity of $6.4 \times 10^{10}$ $M^{-1}$ or more and an antibody binding to rat IgG2c with an avidity of $9.5 \times 10^{10}$ $M^{-1}$ or more,
  c) optionally incubating said sample with a reagent appropriate for the selective detection of total, active or antigen-bound rat antibody, and
  d) correlating the complex formed in (b) or (c) to the concentration of the rat antibody in the sample.

2 Claims, 3 Drawing Sheets

SPECIFIC DETECTION OF RAT ANTIBODIES IN MOUSE SERUM

CROSS-REFERENCE TO RELATED APPLICATIONS

This application is a continuation of International Patent Application No. PCT/EP2014/055462, having an international filing date of Mar. 19, 2014, the entire contents of which are incorporated herein by reference, and which claims benefit under 35 U.S.C. § 119 to European Patent Application No. 13160143.7, filed on Mar. 20, 2013.

The present invention reports the use of a mixture of monoclonal antibodies as capture and tracer antibodies in an immunoassay for measuring the concentration of total, active, or antigen-bound rat antibody in a sample obtained from a mouse.

BACKGROUND OF THE INVENTION

A quite significant number of monoclonal antibodies is under investigation and needs to be studied in experimental animals, before entry into human can be considered for the first trial purposes. Important criteria like bio-availability and antibody clearance just to mention two of them have to be studied. Many of these studies require the quantification of the antibody in the background of the experimental animal's own antibodies. In most cases mammals are used as experimental animals. Toxicology often is first assessed in rodents like mice or rats.

Mammals usually have between about 10 to about 30 milligram of antibody per ml in the circulation. Monoclonal antibodies typically have to be tested with serum levels ranging from about between 1 nanogram per ml to about 100 microgram per ml. The antibody in question, thus, has to be detected against a background of experimental animal's antibodies which are in an excess of about 100-fold to 10 million-fold.

The detection of an antibody derived from a different species than the experimental animal in the background of an experimental animal's antibody represents quite a significant task to the pharmacologist.

In WO 2008/031532 an anti-drug antibody assay is reported. The detection of a therapeutic antibody in an experimental animal is reported in WO 2006/066912. In U.S. Pat. No. 5,332,665 species specific, high affinity monoclonal antibodies are reported. Non-cross reactive anti-IgG antibodies are reported in WO 2011/048043.

SUMMARY OF THE INVENTION

One aspect as reported herein is the use of a mixture of monoclonal antibodies as capture and tracer antibodies in an immunoassay for measuring the concentration of total, active, or antigen-bound rat antibody in a sample obtained from a mouse.

One aspect as reported herein is a method for detecting a rat antibody in a serum or plasma sample (obtained) from a mouse comprising the steps of
a) providing the sample to be analyzed,
b) incubating said serum or plasma sample with an antibody that specifically binds to rat IgG and that does not specifically bind to mouse IgG, for example MAR (K+L) or MRGCOC-1,
c) optionally incubating said sample with a reagent appropriate for the selective detection of total, active or antigen-bound rat antibody, and
d) correlating the complex formed in (b) or (c) to the concentration of the rat antibody in the sample.

One aspect as reported herein is a method for detecting a rat antibody in a serum or plasma sample (obtained) from a mouse comprising the steps of
a) providing the sample to be analyzed,
b) incubating said serum or plasma sample with an antibody that specifically binds to rat IgG and that does not specifically bind to mouse IgG,
wherein the antibody is
  i) a mixture of an antibody binding to rat kappa light chain and an antibody binding to rat lambda light chain, or
  ii) a mixture of an antibody binding to rat IgG1 with an avidity of $4.1 \times 10^{10}$ $M^{-1}$ or more, an antibody binding to rat IgG2a with an avidity of $8.6 \times 10^{9}$ $M^{-1}$ or more, an antibody binding to rat IgG2b with an avidity of $6.4 \times 10^{10}$ $M^{-1}$ or more and an antibody binding to rat IgG2c with an avidity of $9.5 \times 10^{10}$ $M^{-1}$ or more,
c) optionally incubating said sample with a reagent appropriate for the selective detection of total, active or antigen-bound rat antibody, and
d) correlating the complex formed in (b) or (c) to the concentration of the rat antibody in the sample.

One aspect as reported herein is a method for detecting a rat antibody in a serum or plasma sample (obtained) from a mouse comprising the steps of
a) incubating said serum or plasma sample with an antibody binding to the same epitope as antibodies MAR(K+L) or MRGCOC-1,
b) optionally incubating said serum or plasma sample with a reagent appropriate for the selective detection of total, active or antigen-bound therapeutic antibody, and
c) correlating the complex formed in (a) or (b) to the presence and/or concentration of said therapeutic antibody.

One aspect as reported herein is a method for detecting a rat antibody in a serum or plasma sample (obtained) from a mouse comprising the steps of
a) incubating said serum or plasma sample with an antibody which is a mixture of monoclonal antibodies binding to at least two different epitopes,
b) optionally incubating said serum or plasma sample with a reagent appropriate for the selective detection of total, active or antigen-bound therapeutic antibody, and
c) correlating the complex formed in (a) or (b) to the presence and/or concentration of said therapeutic antibody.

One aspect as reported herein is a method for detecting a rat antibody in a serum or plasma sample (obtained) from a mouse comprising the steps of
a) incubating said serum or plasma sample with a capture antibody conjugated to a solid phase and thereby forming a capture antibody-rat antibody complex,
b) incubating the complex the formed in (a) with a tracer antibody and thereby correlating the complex formed in (a) to the presence or concentration of said rat antibody,
wherein the capture antibody is a mixture of monoclonal antibodies binding to at least two different epitopes.

In one embodiment of all aspects the capture antibody and the tracer antibody are each a mixture of monoclonal antibodies binding to at least two different epitopes.

In one embodiment of all aspects the capture antibody is a mixture of monoclonal antibodies binding to the same epitope as antibody MAR(K+L) or antibody MRGCOC-1.

In one embodiment of all aspects the capture antibody is
  i) a mixture of an antibody binding to rat kappa light chain and an antibody binding to rat lambda light chain, or
  ii) a mixture of an antibody binding to rat IgG1 with an avidity of $4.1 \times 10^{10}$ $M^{-1}$ or more, an antibody binding to rat IgG2a with an avidity of $8.6 \times 10^{9}$ $M^{-1}$ or more, an antibody binding to rat IgG2b with an avidity of $6.4 \times 10^{10}$ $M^{-1}$ or more and an antibody binding to rat IgG2c with an avidity of $9.5 \times 10^{10}$ $M^{-1}$ or more.

In one embodiment of all aspects the tracer antibody is a mixture of monoclonal antibodies binding to the same epitope as antibody MAR(K+L) or antibody MRGCOC-1.

In one embodiment of all aspects the tracer antibody is
  i) a mixture of an antibody binding to rat kappa light chain and an antibody binding to rat lambda light chain, or
  ii) a mixture of an antibody binding to rat IgG1 with an avidity of $4.1 \times 10^{10}$ $M^{-1}$ or more, an antibody binding to rat IgG2a with an avidity of $8.6 \times 10^{9}$ $M^{-1}$ or more, an antibody binding to rat IgG2b with an avidity of $6.4 \times 10^{10}$ $M^{-1}$ or more and an antibody binding to rat IgG2c with an avidity of $9.5 \times 10^{10}$ $M^{-1}$ or more.

In one embodiment of all aspects the tracer antibody and the capture antibody are independently of each other a mixture of monoclonal antibodies binding to the same epitope as antibody MAR(K+L) or antibody MRGCOC-1.

In one embodiment of all aspects the tracer antibody and the capture antibody are independently of each other
  i) a mixture of an antibody binding to rat kappa light chain and an antibody binding to rat lambda light chain, or
  ii) a mixture of an antibody binding to rat IgG1 with an avidity of $4.1 \times 10^{10}$ $M^{-1}$ or more, an antibody binding to rat IgG2a with an avidity of $8.6 \times 10^{9}$ $M^{-1}$ or more, an antibody binding to rat IgG2b with an avidity of $6.4 \times 10^{10}$ $M^{-1}$ or more and an antibody binding to rat IgG2c with an avidity of $9.5 \times 10^{10}$ $M^{-1}$ or more.

One aspect as reported herein is a method for detecting a rat antibody in a serum or plasma sample obtained from a mouse comprising the steps of
  a) incubating said serum or plasma sample with a capture antibody conjugated to a solid phase and thereby forming a capture antibody-rat antibody complex,
  b) incubating the complex formed in (a) with a tracer antibody and thereby correlating complex formed in (a) to the presence or concentration of said rat antibody,
wherein the capture antibody is a mixture of monoclonal antibodies binding to the same epitope as antibody MAR(K+L) or antibody MRGCOC-1.

One aspect as reported herein is a method for detecting a rat antibody in a serum or plasma sample (obtained) from a mouse comprising the steps of
  a) incubating said serum or plasma sample with a capture antibody conjugated to a solid phase and thereby forming a capture antibody-rat antibody complex,
  b) incubating the complex formed in (a) with a tracer antibody and thereby correlating complex formed in (a) to the presence or concentration of said rat antibody,
wherein the capture antibody is
  i) a mixture of an antibody binding to rat kappa light chain and an antibody binding to rat lambda light chain, or
  ii) a mixture of an antibody binding to rat IgG1 with an avidity of $4.1 \times 10^{10}$ $M^{-1}$ or more, an antibody binding to rat IgG2a with an avidity of $8.6 \times 10^{9}$ $M^{-1}$ or more, an antibody binding to rat IgG2b with an avidity of $6.4 \times 10^{10}$ $M^{-1}$ or more and an antibody binding to rat IgG2c with an avidity of $9.5 \times 10^{10}$ $M^{-1}$ or more.

One aspect as reported herein is a method for detecting a rat antibody in a serum or plasma sample obtained from a mouse comprising the steps of
  a) incubating said serum or plasma sample with a capture antibody conjugated to a solid phase and thereby forming a capture antibody-rat antibody complex,
  b) incubating the complex formed in (a) with a tracer antibody and thereby correlating complex formed in (a) to the presence or concentration of said rat antibody,
wherein the tracer antibody is a mixture of monoclonal antibodies binding to the same epitope as antibody MAR(K+L) or antibody MRGCOC-1.

One aspect as reported herein is a method for detecting a rat antibody in a serum or plasma sample (obtained) from a mouse comprising the steps of
  a) incubating said serum or plasma sample with a capture antibody conjugated to a solid phase and thereby forming a capture antibody-rat antibody complex,
  b) incubating the complex formed in (a) with a tracer antibody and thereby correlating complex formed in (a) to the presence or concentration of said rat antibody,
wherein the tracer antibody is
  i) a mixture of an antibody binding to rat kappa light chain and an antibody binding to rat lambda light chain, or
  ii) a mixture of an antibody binding to rat IgG1 with an avidity of $4.1 \times 10^{10}$ $M^{-1}$ or more, an antibody binding to rat IgG2a with an avidity of $8.6 \times 10^{9}$ $M^{-1}$ or more, an antibody binding to rat IgG2b with an avidity of $6.4 \times 10^{10}$ $M^{-1}$ or more and an antibody binding to rat IgG2c with an avidity of $9.5 \times 10^{10}$ $M^{-1}$ or more.

In one embodiment of all aspects the method is an antigen bridging immunoassay.

In one embodiment the immunoassay is a sandwich immunoassay.

One aspect as reported herein is a method for immunologically determining a rat antibody in a sample obtained from a mouse using an antigen bridging immunoassay comprising a capture antibody and a tracer antibody, wherein the capture antibody and the tracer antibody are both independently selected from antibodies binding to the same epitope as antibodies MAR(K+L) or MRGCOC-1.

One aspect as reported herein is a method for immunologically determining a rat antibody in a sample (obtained) from a mouse using an antigen bridging immunoassay comprising a capture antibody and a tracer antibody, wherein the capture antibody and the tracer antibody are both independently selected from
  i) a mixture of an antibody binding to rat kappa light chain and an antibody binding to rat lambda light chain, or
  ii) a mixture of an antibody binding to rat IgG1 with an avidity of $4.1 \times 10^{10}$ $M^{-1}$ or more, an antibody binding to rat IgG2a with an avidity of $8.6 \times 10^{9}$ $M^{-1}$ or more, an antibody binding to rat IgG2b with an avidity of $6.4 \times 10^{10}$ $M^{-1}$ or more and an antibody binding to rat IgG2c with an avidity of $9.5 \times 10^{10}$ $M^{-1}$ or more.

In one embodiment the conjugation of the antibody to its conjugation partner is performed by chemically binding via N-terminal and/or ε-amino groups (lysine), ε-amino groups of different lysines, carboxy-, sulfhydryl-, hydroxyl- and/or phenolic functional groups of the amino acid backbone of the antibody and/or sugar alcohol groups of the carbohydrate structure of the antibody.

In one embodiment the capture antibody is immobilized via a specific binding pair. In one embodiment the capture antibody is conjugated to biotin and immobilization is performed via immobilized avidin or streptavidin.

In one embodiment the tracer antibody is conjugated to the detectable label via a specific binding pair. In one embodiment the tracer antibody is conjugated to digoxygenin and linking to the detectable label is performed via an antibody against digoxygenin.

In another embodiment of all aspects the rat antibody is a Fab.

In one embodiment of all aspects the rat antibody is a monoclonal antibody.

In one embodiment the total therapeutic antibody is detected, in another the active therapeutic antibody is detected, and in a further the therapeutic antibody is detected which is bound to its antigen.

One aspect as reported herein is the use of an antibody which is specifically binding to a rat antibody and not binding to the immunoglobulin of a mouse for determining the concentration of total, active, or antigen-bound rat antibody in a sample obtained from a mouse whereby the antibody is binding to the same epitope as antibodies MAR (K+L) or MRGCOC-1.

One aspect as reported herein is the use of an antibody which is specifically binding to a rat antibody and not binding to the immunoglobulin of a mouse for determining the concentration of total, active, or antigen-bound rat antibody in a sample obtained from a mouse whereby the antibody is
  i) a mixture of an antibody binding to rat kappa light chain and an antibody binding to rat lambda light chain, or
  ii) a mixture of an antibody binding to rat IgG1 with an avidity of $4.1 \times 10^{10}$ $M^{-1}$ or more, an antibody binding to rat IgG2a with an avidity of $8.6 \times 10^{9}$ $M^{-1}$ or more, an antibody binding to rat IgG2b with an avidity of $6.4 \times 10^{10}$ $M^{-1}$ or more and an antibody binding to rat IgG2c with an avidity of $9.5 \times 10^{10}$ $M^{-1}$ or more.

One aspect as reported herein is the use of a mixture of monoclonal antibodies binding to at least two different epitopes of a rat antibody as capture antibody in an immunoassay for measuring the concentration of total, active, or antigen-bound rat antibody in a serum or plasma sample obtained from a mouse.

One aspect as reported herein is the use of a mixture of monoclonal antibodies binding to at least two different epitopes of a rat antibody as capture antibody and a tracer antibody in an immunoassay for measuring the concentration of total, active, or antigen-bound rat antibody in a serum or plasma sample obtained from a mouse.

DETAILED DESCRIPTION OF THE INVENTION

The term "rat antibody" denotes an antibody that has been derived from a rat after immunization with the respective antigen. The rat antibody can be modified to be a "therapeutic antibody" which is intended to be tested in clinical studies for approval as human therapeutic and which can be administered to an individual for the treatment of a disease. In one embodiment the rat antibody is a monoclonal antibody. Therapeutic antibodies are being used widely for the treatment of various diseases such as oncological diseases (e.g. hematological and solid malignancies including non-Hodgkin's lymphoma, breast cancer, and colorectal cancer), immunological diseases, central nervous diseases, vascular diseases, or infectious diseases. Such antibodies are, for instance, antibodies against CD20, CD22, HLA-DR, CD33, CD52, EGFR, G250, GD3, HER2, PSMA, CD56, VEGF, VEGF2, CEA, Levis Y antigen, IL-6 receptor (IL6R), or IGF-1 receptor (IGF1R).

The term "antibody" encompasses the various forms of antibody structures including whole antibodies and antibody fragments. Genetic engineering of antibodies is e.g. described in Morrison, S. L., et al., Proc. Natl. Acad Sci. USA 81 (1984) 6851-6855; U.S. Pat. Nos. 5,202,238 and 5,204,244; Riechmann, L., et al., Nature 332 (1988) 323-327; Neuberger, M. S., et al., Nature 314 (1985) 268-270; Lonberg, N., Nat. Biotechnol. 23 (2005) 1117-1125.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations, which include different antibodies directed against different antigenic sites (determinants or epitopes), each monoclonal antibody is directed against a single antigenic site on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies and is not to be construed as requiring production of the antibody by any particular method.

The term "mixture of monoclonal antibodies" as used herein denotes an antibody composition that consist of more than one different monoclonal antibodies each of which is binding to different epitopes of the same antigen. In one embodiment the mixture comprises antibodies binding to two or more different epitopes of the same antigen. In one embodiment the mixture comprises antibodies binding to two to ten different epitopes of the same antigen. In one embodiment the mixture comprises antibodies binding to two to four different epitopes of the same antigen.

The term "sample" denotes any tissue or liquid sample removed from an experimental animal. In one embodiment the sample will be a liquid sample like saliva, urine, whole blood, plasma or serum. In a further embodiment the sample will be whole blood, plasma or serum.

An "antibody binding to a rat antibody and not binding to the antibody of a mouse" will bind to a rat antibody with a dissociation constant (=$K_{Diss}$) of at least $10^{-9}$ mol/l. In one embodiment the $K_{Diss}$ is at least $10^{-10}$ mol/l. At the same time the property of not binding to the antibody of a mouse is insured by a $K_{Diss}$ of $10^{-7}$ mol/l or worse. In one embodiment the antibody binding to a rat antibody and not binding to the antibody of a mouse will have a $K_{Diss}$-gap of at least 100-fold between its reactivity towards the immunoglobulin of class G of a mouse and towards rat immunoglobulin of class G, respectively.

Generally the term "binding to" denotes that an antibody binds to its antigen or the corresponding antibody receptor, whichever is intended in the respective context, with a dissociation constant (=$K_D$=$K_{Diss}$ of $10^{-9}$ mol/l or less, in another embodiment with a $K_D$ of at least $10^{-10}$ mol/l. At the same time the property of not binding is insured by a $K_D$ of $10^{-7}$ mol/l or more (e.g. $10^{-5}$ mol/l). Also in one embodiment the antibody binding to a first antibody and not binding to a second antibody will have a $K_D$-gap of at least 100-fold between its reactivity towards the first immunoglobulin of class G and towards the second immunoglobulin of class G.

The binding properties of an antibody, especially the $K_{Diss}$, in one embodiment are assessed by surface plasmon resonance on a BIAcore® instrument. In this method binding properties are evaluated by changes in surface plasmon resonance (SPR). It is convenient to bind the antibody under investigation to the solid phase (called chip) and to assess binding of a monoclonal antibody, a polyclonal antibody or even of serum comprising IgG to this coated chip.

Various aspects connected to the application of a rat antibody in a mouse may have to be assessed. In certain settings it may be relevant to analyze the total amount of rat antibody present, or it may be important to analyze certain fragments of a rat antibody, or certain modifications of a rat antibody, or the concentration of rat antibody bound to an antigen, or the fraction of a rat antibody still capable of binding to an antigen. In one embodiment the antibodies and methods as reported herein can be used to detect the total, active, or antigen-bound rat antibody in a mouse, respectively.

The term "total antibody" denotes any antibody detected irrespective of whether the antibody is active (i.e. still reactive with its antigen), inactive, and/or antigen-bound.

The term "active antibody" denotes the rat antibody present in a mouse that still is capable of binding its antigen. Such antibodies, e.g., have not bound its antigen or any other molecule at its antigen binding site.

The term "antigen-bound antibody" denotes the rat antibody as present in the circulation of a mouse that is bound to its antigen.

Total, active, or antigen-bound (rat) antibody as defined above can be directly detected with the antibodies and in methods as reported herein. Additionally it is possible to detect other forms of non-active rat antibodies, such as rat antibodies bound by anti-drug antibodies or anti-idiotype antibodies or especially neutralizing anti-drug antibodies (e.g. endogenous anti-drug antibodies (ADA)).

In addition, it is also possible to indirectly assess any "inactive antibody". Such inactive (rat) antibody may, e.g., be a rat antibody bound to its antigen, or the rat antibody bound to a cross-reactive antigen, or the rat antibody blocked by an auto or anti-idiotypic antibody against the rat antibody. In case the total antibody amounts to more than the sum of active antibody and antigen-bound antibody, an additional fraction of antibody comprising the inactive antibody not bound to its corresponding antigen will be present.

Total (rat) antibody for example can be detected in a so-called competitive immunoassay system or in a so-called sandwich type assay system. Such assay may be performed in one embodiment without washing steps (homogeneous immunoassay) or in another embodiment with washing steps (heterogeneous immunoassay).

In one embodiment the total (rat) antibody is detected in a sandwich type immunoassay, wherein the antibody which is binding to a rat antibody and not binding to the antibody of a mouse is used at both sides of such a sandwich assay. The antibody used at one side of such sandwich is bound or capable of binding to a solid phase (often referred to as capture antibody), whereas the antibody at the other side of such sandwich is labeled in such a manner that direct or indirect detection is facilitated (so-called tracer or detection antibody). The amount of tracer/detection antibody bound in such a sandwich assay procedure is directly correlated to the amount of rat antibody in the sample investigated.

Detection of active (rat) antibody in a sample may be achieved by convenient state of the art procedures. However, the detection of total (rat) antibody or of the fraction of (rat) antibody bound to its antigen is rather complicated and requires quite different assay set-ups and especially requires tailor-made reagents for each of the different assays. With the antibodies as reported herein which are binding to a rat antibody and not binding to the antibody of a mouse it is possible to assess the fraction of active rat antibody, total rat antibody, or antigen-bound rat antibody in test systems which are analogues to each other. This kind of comparative assessment of total, active, or antigen-bound rat antibody should have advantages once quantitative comparisons are made in between these various fractions of therapeutic antibody.

In one embodiment a sandwich type assay format is set up to detect the active (rat) antibody. In a further embodiment the antibody which is binding to a rat antibody and not binding to the antibody of a mouse is used as a capture antibody and the detection side of such sandwich assay either makes use of the antigen in a labeled form or after binding of the antigen makes use of a second antibody not binding to or competing with the epitope recognized by the rat antibody, wherein the second antibody is specifically detectable and/or is labeled in such a manner that direct or indirect detection is facilitated.

The antigen-bound (rat) antibody in one embodiment is detected in a sandwich type assay format using the antibody binding to a rat antibody and not binding to the antibody of a mouse as a capture reagent. In the detection in one embodiment a second antibody is used binding to the antigen at an epitope which does not compete with the epitope of the rat antibody. The second antibody is in one embodiment labeled in such a manner that direct or indirect detection is facilitated.

For direct detection the labeling group can be selected from any known detectable marker groups, such as dyes, luminescent labeling groups such as chemiluminescent groups, e.g. acridinium esters or dioxetanes, or fluorescent dyes, e.g. fluorescein, coumarin, rhodamine, oxazine, resorufin, cyanine and derivatives thereof. Other examples of labeling groups are luminescent metal complexes, such as ruthenium or europium complexes, enzymes, e.g. as used for ELISA or for CEDIA (Cloned Enzyme Donor Immunoassay), and radioisotopes. Metal chelates which can be detected by electrochemiluminescence are also in one embodiment signal-emitting groups used as detectable labels, with particular preference being given to ruthenium chelates. In one embodiment the labeling group is a ruthenium (bispyridyl)$_3^{2+}$ chelate.

Indirect detection systems comprise, for example, that the detection reagent, e.g. the tracer/detection antibody, is labeled with a first partner of a binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g., steroid hormone receptor/steroid hormone. In one embodiment the first binding pair member is selected from hapten, antigen and hormone. In one embodiment the hapten is selected from digoxin and biotin and analogues thereof The second partner of such binding pair, e.g. an antibody, streptavidin, etc., usually is labeled to allow for direct detection, e.g., by the labels as mentioned above.

In all the above immunological detection methods reagent conditions are chosen which allow for binding of the reagents employed, e.g. for binding of an antibody to its corresponding antigen. The skilled artisan refers to the result of such binding event by using the term complex. The complex formed in an assay method as reported herein is correlated by state of the art procedures to the corresponding concentration of the therapeutic antibody. Such a correlation can be made e.g. by way of preparing and determining the complex in a dilution series of the corresponding complex with the method as reported herein and by correlating the obtained result with the concentration of the individual complex components. Depending on the detection reagent employed this correlating step will result in the concentration of total, active, or antigen-bound therapeutic antibody.

As the skilled artisan will appreciate the methods as reported herein will not only reveal the concentrations of total, antigen-bound, active or even inactive (rat) antibody. Due to the use of one and the same reagent, the antibody binding to a rat antibody and not binding to the antibody of a mouse, in the different assays the values obtained can be easily compared to each other and even ratios thereof assessed. In a further embodiment the present method relates to the ratio of active to total (rat) antibody. This ratio may well serve as an indicator for the efficacy of a (rat) antibody.

For determining the binding to the same or an overlapping epitope, for example, a method can be used in which epitope overlapping of two antibodies binding to the same target antigen is determined with the help of a competitive test system. For this purpose, for example with the help of an enzyme immunoassay, there is tested the extent to which the antibody in question competes with the known antibody for the binding to an immobilized target antigen, e.g. employing an antibody produced by one of the cell lines as reported herein. For this purpose, an appropriately immobilized target antigen is incubated with the known antibody in labeled form and an excess of the antibody in question. By detection of the bound labeling there can easily be ascertained the extent to which the antibody in question can displace the known antibody from the binding. If there is a displacement of more than 20%, in another embodiment of more than 30%, at the same concentration or a displacement of more than 70%, in another embodiment of more than 80%, at higher concentrations, in one embodiment in the case of $10^3$-$10^5$-fold excess of the antibody in question, referred to the known antibody, then epitope overlapping is present and both antibodies bind to the same or an overlapping part of the same epitope.

The specificity of the antibodies can be shown in a sandwich-ELISA employing each a biotinylated and a digoxygenylated variant of the respective antibodies and serum from different species. To be a generally applicable assay for detection and quantification of rat IgG in the serum of a mouse, such an assay requires an anti-rat IgG antibody whose binding site is independent from any secondary antibody modification, such as e.g. glycosylation or deamidation. Otherwise it would be necessary to optimize the assay for each new rat antibody to be detected and quantified.

The specificity of antibodies can also be shown in a surface plasmon resonance experiment using the BIAcore technology.

One aspect as reported herein is an assay for quantifying a rat antibody or its derivative such as Fab-fragments in a sample obtained from a mouse comprising a biotinylated mixture of monoclonal antibodies as capture antibody and a digoxygenylated mixture of monoclonal antibodies as tracer antibody. The antibody MARGCOC-1 or MRGCOC-1 (which names can be used interchangeably) is a mixture of an antibody binding to rat IgG1 with an avidity of $4.1 \times 10^{10}$ $M^{-1}$ or more, an antibody binding to rat IgG2a with an avidity of $8.6 \times 10^9$ $M^{-1}$ or more, an antibody binding to rat IgG2b with an avidity of $6.4 \times 10^{10}$ $M^{-1}$ or more and an antibody binding to rat IgG2c with an avidity of $9.5 \times 10^{10}$ $M^{-1}$ or more.

The antibody MAR(K+L) is a mixture of an antibody binding to rat kappa light chain and an antibody binding to rat lambda light chain.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (likewise by Kd or KD or equilibrium constant). Affinity can be measured by common methods known in the art.

"Avidity" refers to the accumulated strength of multiple affinities of individual non-covalent binding interactions such as antigen-antibody interactions. Avidity therefore gives a measure for the overall strength of an antigen-antibody complex.

One aspect as reported herein is an assay comprising a capture and tracer antibody binding specifically to epitopes on different domains of a rat IgG. In this assay only an intact rat antibody will result in a positive assay result and a detectable signal. In one embodiment the capture antibody and the tracer antibody are independently selected from the antibodies as reported herein.

One aspect as reported herein is an assay in which the anti-rat IgG antibody is used as a reference standard and/or positive control to mimic an anti-drug antibody (ADA). This can be useful during assay development to find out optimal assay conditions and test robustness of the assay, i.e. to check assay performance with different standard reagents/positive controls. Especially advantageous is this set-up in view of the fact that an ADA will be polyclonal and probably be directed against both, the Fab fragment and the Fc part.

One aspect as reported herein relates to the use of an antibody which is binding to a rat antibody and not binding to the antibody of a mouse for measuring the concentration of total, active, or antigen-bound rat antibody in a sample obtained from a mouse.

One aspect as reported herein relates to the use of two antibodies which both are binding to a rat antibody and not binding to the antibody of a mouse for measuring the concentration of total, active, or antigen-bound rat antibody in a sample obtained from a mouse, wherein one of the antibodies is the capture antibody and one of the antibodies is the tracer antibody. In one embodiment the rat antibody is a Fab fragment.

In the methods as reported herein also different capture molecules can be used such as complete antibodies, F(ab')$_2$ fragments, Fab fragments or even single chain antibodies.

The methods reported herein are exemplified with an antibody against an antibody against the IL-1R receptor (anti-IL1R antibody) as reported in WO 2005/023872, (incorporated herein by reference).

The following examples and figures are provided to aid the understanding of the present invention, the true scope of which is set forth in the appended claims. It is understood that modifications can be made in the procedures set forth without departing from the spirit of the invention.

EXAMPLE 1

Reactivity of different Anti-Rat IgG Antibodies with Serum of Several Animal Species in an MTP-ELISA A microtiter plate (MTP) (Maxisorb®, Nunc) was coated with serum of different species diluted to 10% in phosphate buffered saline at room temperature (RT) for 1 hour, respectively. Serum from rat, mouse, rabbit, cynomolgus, hamster and guineapig was used. After washing 3 times with PBS-Tween®20, all wells of the MTPs were blocked with PBS/3% BSA at room temperature for 1 hour. Then the wells of the MTPs were incubated (1 h; RT) with different anti-rat IgG antibodies (digoxigenin or horseradish peroxidase conjugates (HRP) (POD)). The anti-Rat antibodies were used as recommended by the corresponding manufacturer.

Figure 1:
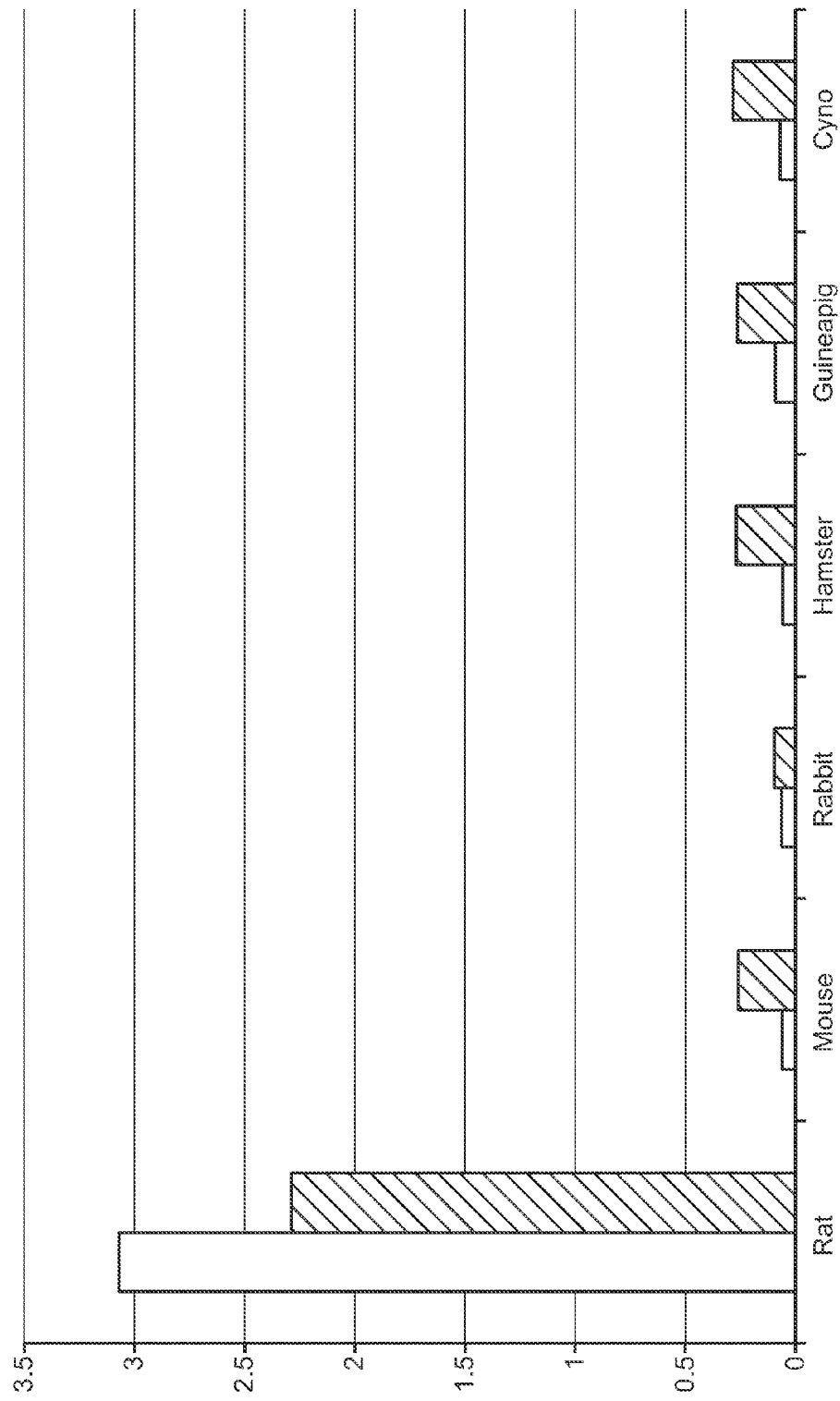
FIG. 1 Reactivity of different Anti-Rat IgG antibodies with serum of several animal species; left bar: MAR(K+L), right bar: Pab anti-rat-HRP (Cell Signaling Technology).
Figure 2:
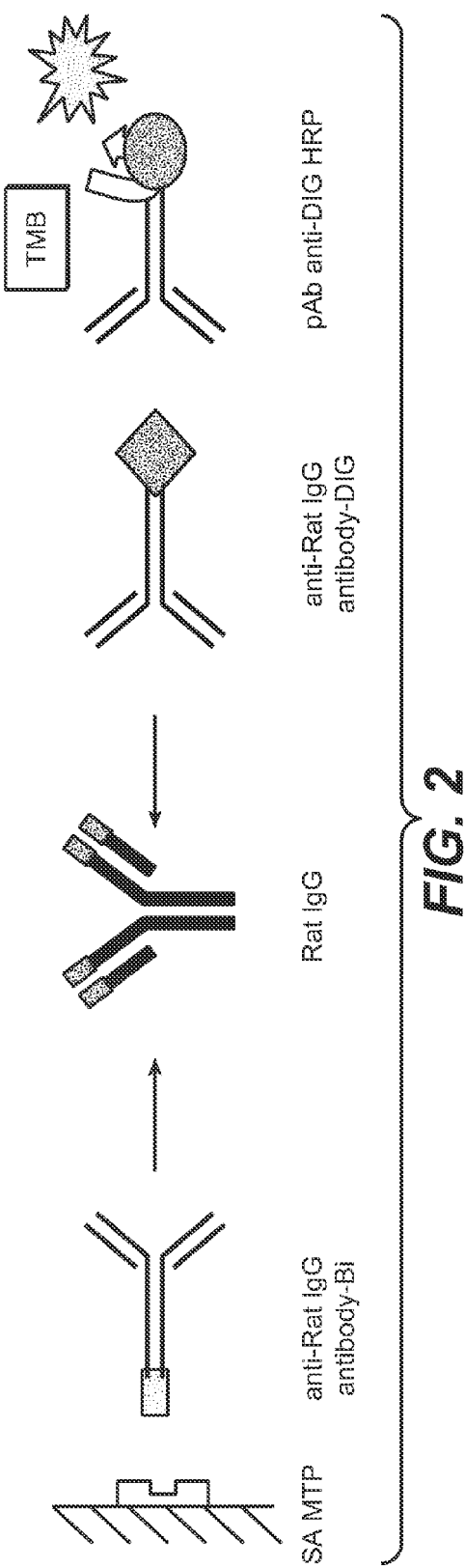
FIG. 2 Schematic assay setup of an exemplary SA-MTP ELISA for quantification of total therapeutic antibody using the method as reported herein.

Wells were washed three times as above. Wells incubated with POD-conjugates were directly processed for enzymatic reaction/detection of bound anti-rat immunoglobulin. The other wells were incubated (1 h; RT) as appropriate with anti-DIG conjugates (all reagents from Roche Diagnostics, Germany) followed by a washing step. The POD comprised in the POD-conjugates catalyzes the color reaction of ABTS substrate. The signal was measured by an ELISA reader at a wavelength of 405 nm (reference wavelength: 490 nm) (see FIG. 1). For every anti-rat IgG antibody the ratios of the signal against rat antibodies to the signal of the other sera were calculated. These values were used for evaluation of the specificity of the anti-Rat IgG antibodies. A high ratio translates to a strong reactivity with rat immunoglobulin and at the same time to a low (cross-) reactivity with immunoglobulin from other species (see table below).

TABLE

|  | MAR(K + L)-DIG | | pAb anti-rat-HRP - | |
| --- | --- | --- | --- | --- |
|  | Signal [OD405 nm] | Signal Ratio Rat/other species | Signal [OD405 nm] | Signal Ratio Rat/other species |
| Rat Serum | 3.074 | 1.0 | 2.292 | 1.0 |
| Mouse Serum | 0.061 | 50.8 | 0.261 | 8.8 |
| Rabbit Serum | 0.062 | 50.0 | 0.099 | 23.3 |
| Hamster Serum | 0.055 | 56.4 | 0.470 | 4.9 |
| Guineapig Serum | 0.094 | 32.9 | 0.266 | 8.6 |
| Cynomolgus Serum | 0.074 | 41.8 | 0.279 | 8.2 |

EXAMPLE 2

Figure 3:
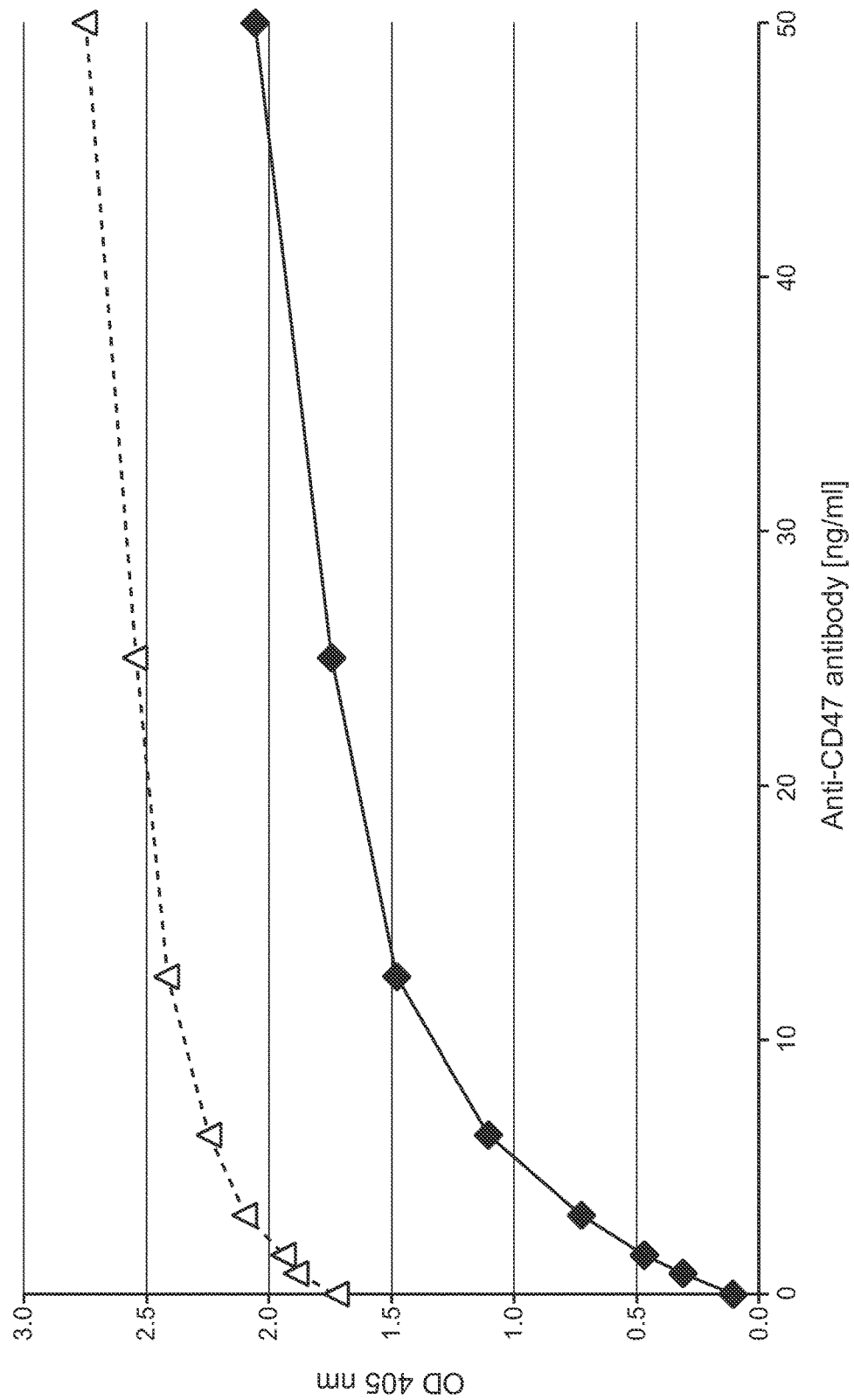
FIG. 3 Comparison of MARGCOC-1 and MAR(K+L) as an example of a mixture of monoclonal antibodies with a polyclonal antibody for quantification of total therapeutic antibody; upper curve (triangles): Pab anti-rat IgG-HRP (Cell Signaling Technology); lower curve (diamonds): MAR (K+L).

Use of Mixtures of Monoclonal Antibodies as Capture and Tracer Antibodies for Quantification of Total Therapeutic Antibody Biotinylated MARGCOC-1 (as example of a mixture comprising 4 monoclonal antibodies binding to different epitopes) was bound to streptavidin-coated microtiter plates (SA-MTP) in the first step. The excess of unbound antibody was removed by washing. Then, samples/standards, e.g. Rat anti-CD47 antibody spiked in Mouse serum, were added and incubated for 1 hour. After washing, the wells were incubated with digoxigenylated MAR(K+L) (as example of a mixture comprising 2 monoclonal antibodies binding to different epitopes) or HRP labeled pAb anti-Rat-IgG (Cell Signaling Technology). After washing the bound digoxigenylated MAR(K+L) was detected with an anti-digoxigenin antibody HRP conjugate. The HRP of the antibody-enzyme conjugates catalyzes the color reaction of ABTS substrate. The signal is measured by ELISA reader at 405 nm wavelength (reference wavelength: 490 nm) (see FIG. 3). Absorbance values of each serum sample were determined in triplicates.

EXAMPLE 3

Use of the Same Mixture of Monoclonal Antibodies as Capture and Tracer Antibodies for Quantification of Total Therapeutic Antibody A microtiter plate (MTP) (Maxisorb®, Nunc) was coated with 10 µg/mL of MAR(K+L) and Pab anti-rat-IgG (Molecular Probes #A10536) in the first step. The excess of unbound antibody was removed by washing. Then, samples/standards, e.g. mAb anti-CD47-rat-IgG spiked in mouse serum and also diluted in buffer were added to and incubated for 1 hour. After washing, the wells were incubated with digoxigenylated MAR(K+L) or HRP labeled Pab anti-rat-IgG (Molecular Probes #A10549). After washing, the bound digoxigenylated MAR(K+L) was detected with an anti-digoxigenin-antibody HRP conjugate. The other detection antibody already had the HRP label, so no second detection antibody was needed prior to Substrate incubation. The HRP of the antibody-enzyme conjugates catalyzes the color reaction of ABTS substrate. The signal is measured by ELISA reader at 405 nm wavelength (reference wavelength: 490 nm). Absorbance values of each serum sample were determined in triplicates.

What is claimed is:

1. Method for detecting a rat antibody in a serum or plasma sample obtained from a mouse comprising the steps of
   a) providing the sample to be analyzed,
   b) incubating said serum or plasma sample with an antibody that specifically binds to rat IgG and that does not specifically bind to mouse IgG,
      wherein the antibody is
      i) a mixture of a monoclonal antibody binding to rat kappa light chain and a monoclonal antibody binding to rat lambda light chain, or
      ii) a mixture of a monoclonal antibody binding to rat IgG1 with an avidity of $4.1 \times 10^{10}$ $M^{-1}$ or more, a monoclonal antibody binding to rat IgG2a with an avidity of $8.6 \times 10^9$ $M^{-1}$ or more, a monoclonal antibody binding to rat IgG2b with an avidity of $6.4 \times 10^{10}$ $M^{-1}$ or more and a monoclonal antibody binding to rat IgG2c with an avidity of $9.5 \times 10^{10}$ $M^{-1}$ or more,
      wherein the antibody that specifically binds to rat IgG and that does not specifically bind to mouse IgG binds to the same epitope as antibody MAR(K+L) or antibody MRGCOC-1, and
   c) correlating the complex formed in (b) to the concentration of the rat antibody in the sample.

2. The method according to claim 1, wherein said rat antibody is a Fab.

\* \* \* \* \*